United States Patent
Mainx et al.

(10) Patent No.: US 8,980,867 B2
(45) Date of Patent: Mar. 17, 2015

(54) BIOCIDE COMPOSITIONS COMPRISING ALKOXYLATED OLIGOGLYCEROL ESTERS

(75) Inventors: Hans-Georg Mainx, Leichlingen (DE); Sandra Mack, Korschenbroich (DE); Ingo Fleute-Schlachter, Essen (DE)

(73) Assignee: Cognis IP Management GmbH, Duesseldorf (DE)

( * ) Notice: Subject to any disclaimer, the term of this patent is extended or adjusted under 35 U.S.C. 154(b) by 15 days.

(21) Appl. No.: 13/696,891

(22) PCT Filed: Mar. 30, 2011

(86) PCT No.: PCT/EP2011/001579
§ 371 (c)(1),
(2), (4) Date: Nov. 8, 2012

(87) PCT Pub. No.: WO2011/141093
PCT Pub. Date: Nov. 17, 2011

(65) Prior Publication Data
US 2013/0053349 A1    Feb. 28, 2013

(30) Foreign Application Priority Data

May 8, 2010  (EP) .................................... 10004859

(51) Int. Cl.
  *A01N 57/16*  (2006.01)
  *A01P 7/04*   (2006.01)
  *A01N 43/54*  (2006.01)
  *A01P 3/00*   (2006.01)
  *A01N 43/653* (2006.01)
  *A01N 37/36*  (2006.01)
  *A01N 25/30*  (2006.01)

(52) U.S. Cl.
  CPC .............. *A01N 43/653* (2013.01); *A01N 25/30* (2013.01); *A01N 43/54* (2013.01); *A01N 57/16* (2013.01)
  USPC .............. 514/89; 514/383; 514/532; 514/269

(58) Field of Classification Search
  None
  See application file for complete search history.

(56) References Cited

U.S. PATENT DOCUMENTS

| | | | |
|---|---|---|---|
| 6,413,908 B1 * | 7/2002 | Reekmans et al. | 504/363 |
| 7,709,011 B2 * | 5/2010 | Klug et al. | 424/400 |
| 2004/0171492 A1 | 9/2004 | Mainx et al. | |
| 2006/0264330 A1 | 11/2006 | Zerrer et al. | |

FOREIGN PATENT DOCUMENTS

| | | |
|---|---|---|
| DE | 10000320 | 7/2001 |
| EP | 0539980 | 5/1993 |
| EP | 539980 A1 * | 5/1993 |
| WO | WO-01/08481 | 2/2001 |
| WO | WO-03003830 | 1/2003 |
| WO | WO-2004/073404 | 9/2004 |

OTHER PUBLICATIONS

Rubin, Pure Oleic Acid from Olive Oil, The Journal of The American Oil Chemists' Society, 1960, 37, pp. 300-302.*
"International Search Report in PCT/EP2011/001579", mailed on May 23, 2011, 3 pgs.
"European Search Report in EP10004859.4", dated Feb. 7, 2011, 2 pgs.

* cited by examiner

*Primary Examiner* — Melenie McCormick
*Assistant Examiner* — Andrew Lee
(74) *Attorney, Agent, or Firm* — Servilla Whitney LLC

(57) ABSTRACT

Suggested are biocide compositions, comprising (a) Alkoxylated oligoglycerol esters; (b) Biocides and optionally (c) Oil components or co-solvents and/or (d) Emulsifiers. The compositions show excellent adjuvant properties.

12 Claims, No Drawings

BIOCIDE COMPOSITIONS COMPRISING ALKOXYLATED OLIGOGLYCEROL ESTERS

CROSS-REFERENCE TO RELATED APPLICATIONS

This application is the national stage entry of PCT/EP2011/001579, filed on Mar. 30, 2011, which claims priority to European Application No. 10004859.4, filed on May 8, 2010, the disclosures of which are incorporated herein by reference in their entireties.

FIELD OF THE INVENTION

The present invention relates to the area of agrochemicals and refers to biocide compositions comprising alkoxylated oligoglycerol esters and their use as adjuvants for biocides.

BACKGROUND OF THE INVENTION

Biocides, and in particular pesticides such as fungicides, insecticides and herbicides, are important auxiliary agents for agriculture in order to protect crops and to increase their quality and harvest yield. Depending on the various and often very specific needs, a magnitude of actives exists showing very different chemical structures and behaviours. Nevertheless, it is well known from the state of the art that it remains difficult to prepare liquid compositions of these actives which are exhibiting a satisfying stability, especially if stored at very low or elevated temperatures over a longer period. In addition to storage stability and the ability to prepare stable tank mixes, the influence of additives and adjuvants on bioperformance is of elevated importance. Their choice is governed by many additional parameters, such as ease to manufacture, a low toxicological and eco-toxicological profile, their compatibility such formulations such as emulsifiable concentrates (EC), oil in water emulsions (EW), suspo-emulsions (SE) and concentrated suspensions in water (SC) or in oil (OD)

Ethoxylated polyol esters are known as additives and adjuvants in agrochemical applications for a long time. For example DD 268147 A1 describes the use of ethoxylated soy bean oil as an adjuvant for herbicides, especially bromoxynil potassium salt. WO 96/022109 A1 (SEPPIC) claims a group of ethoxylated polyol esters as ingredients for pesticide and pharmaceutical formulations. Finally, EP 0539980 B1 and EP 0765602 B1, both assigned to Kao, disclose di- and oligoglycerol esters in combination with other nonionic surfactants as adjuvants in particular for herbicides and plant growth promoters. However, none of these adjuvants exhibit over a broad spectrum of different biocides a satisfying performance.

Therefore, the problem underlying the present invention has been to overcome the disadvantages of the state of the art. In particular it has been the object to provide new additives for agricultural compositions combining superior adjuvant properties in order to support and increase the performance of various biocides and high stability of the compositions also over longer storage times and different storage temperatures.

DETAILED DESCRIPTION OF THE INVENTION

The present invention refers to biocide compositions, comprising
(a) Alkoxylated oligoglycerol esters,
(b) Biocides and optionally
(c) Oil components and/or co-solvents and/or
(d) Emulsifiers.

Surprisingly it has been observed that alkoxylated oligoglycerol esters, and in particular ethoxylated diglycerol esters based on unsaturated fatty acids exhibiting superior adjuvant performance compared to similar non-alkoxylated compounds The products improve the weed control properties of many aqueous biocide formulations, especially of well known biocides like for example glyphosate or epoxiconazole. Compositions comprising alkoxylated oligoglycerol esters according to the present invention also exhibit better storage stability when compared especially with tallow amine ethoxylates.

Alkoxylated Oligoglycerol Esters

Oligolycerol esters and their alkoxylation products represent well known non-ionic surfactants obtainable according to standard procedures of organic chemistry, for example by direct esterification or transesterification of the related alkoxylated oligoglycerol with fatty acids or fatty acid methyl esters. Alkoxylated oligoglycerol esters forming compound (a) of the present invention typically follow general formula (I)

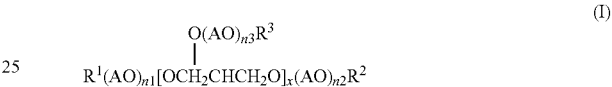

in which $R^1$, $R^2$ and $R^3$ independently represent either hydrogen or a saturated or unsaturated, linear or branched and optionally hydroxy substituted acyl radical having 2 to 22, preferably 6 to 22 and more preferably 16 to 18 carbon atoms and up to three double bonds on condition that at least one of the groups $R^1$, $R^2$ and $R^3$ is different from hydrogen, AO stands for an alkylene oxide unit selected from ethylene oxide, propylene oxide, butylene oxide and their mixtures, n1, n2 and n3 independently mean integers in the range from 1 to about 100 on condition that the sum (n1+n2+n3) is an integer in the range of about 10 to about 200, and x means an integer in the range of 1.1 to 10.

As formula (I) shows, the alkoxylated oligoglycerol esters cover a wide range of species, since the molecule can be tailored by modifying one or more of the following structural features:

Degree of oligomerisation of the glycerol backbone;
Type and degree of alkoxylation;
Type of fatty acid moiety and
Degree of esterification.

Oligoglycerol in the context of the present invention means oligomers of glycerol obtainable for example by alkaline condensation of glycerol under high temperature conditions or polycondensation of epichlorhydrin. The oligomers may be either linear or branched or even cyclic. The average degree of oligomerisation is between 1.1 and 10, preferably 1.5 and 5 and more preferably between 2 and 4. For clarity reasons it should be noted that the degree of oligomerisation represents an average value. For example a degree of oligomerisation of 1.1 means that a mixture was obtained comprising about 90% unreacted glycerol and 10% higher oligomers, in particular diglycerol. Diglycerol esters according to the present invention typically comprise either about 90% diglycerol esters and 10% higher oligomers or a raw mixture of oligomerised glycerol with degree of polymerization between 1 and 6, preferably an average of 2.

As far as the alkylene oxide units are concerned it is stated that one may apply ethoxylates, propoxylates, butoxylates or their mixtures. The polyalkylene glycol chain may comprise these units blockwise or in random distribution. It is possible that the oligoglycerol esters according to the present invention contain up to 200 alkylene oxide units. The preferred species, however, contain between 5 and 50 and more particularly between 10 and 15 alkylene oxide units, preferably ethylene oxide units.

The fatty acids forming the lipophilic part of the molecule can be derived from short chain carboxylic acids or medium or long chain fatty acids, such as acetic acid, propionic acid, butyric acid, capric acid, caprylic acid, capronic acid, lauric acid, myristic acid, palmitic acid, stearic acid, 12-hydroxy stearic acid, isostearic acid, behenic acid and their mixtures. Preferred, however, are unsaturated fatty acids as for example oleic acid, elaidinic acid, linolic acid, linoleic acid, conjugated linoleic acid, ricinoleic acid and their mixtures including technical grade fatty acid mixtures obtained for example from sunflower oil, high-oleic sunflower oil (HOSO), line seed oil, olive oil and the like.

The alkoxylated oligoglycerol esters may be fully esterified or in part. Preferred are species showing a degree of esterification between 1 and 3, in particular of about 2. It should be understood that also the degree of esterification represents an average value. In particular preferred species according to the present invention represent either Diglycerol esters;
Ethoxylated oligoglycerol esters, or
Alkoxylate oligoglycerol esters derived from saturated and unsaturated fatty acids.

Particularly preferred are of course those species combining all three features which means ethoxylated diglycerol esters derived from saturated and unsaturated fatty acids.

Biocides

A biocide, also called bio-active agent (component b) in the context of the present invention is a plant protection agent, more particular a chemical substance capable of killing different forms of living organisms used in fields such as medicine, agriculture, forestry, and mosquito control. Also counted under the group of biocides are so-called plant growth regulators. Usually, biocides are divided into two sub-groups:

pesticides, which includes fungicides, herbicides, insecticides, algicides, moluscicides, miticides and rodenticides, (here, The Pesticide Manual, 14$^{th}$ edition, BCPC 2006 is included as a reference, it provides information about the individual mode of actions of active ingredients) and antimicrobials, which includes germicides, antibiotics, antibacterials, antivirals, antifungals, antiprotozoals and antiparasites.

Biocides can also be added to other materials (typically liquids) to protect the material from biological infestation and growth. For example, certain types of quaternary ammonium compounds (quats) can be added to pool water or industrial water systems to act as an algicide, protecting the water from infestation and growth of algae.

a) Pesticides

The U.S Environmental Protection Agency (EPA) defines a pesticide as "any substance or mixture of substances intended for preventing, destroying, repelling, or mitigating any pest". A pesticide may be a chemical substance or biological agent (such as a virus or bacteria) used against pests including insects, plant pathogens, weeds, mollusks, birds, mammals, fish, nematodes (roundworms) and microbes that compete with humans for food, destroy property, spread disease or are a nuisance. In the following examples, pesticides suitable for the agrochemical compositions according to the present invention are given:

b) Fungicides

A fungicide is one of three main methods of pest control—the chemical control of fungi in this case. Fungicides are chemical compounds used to prevent the spread of fungi in gardens and crops. Fungicides are also used to fight fungal infections. Fungicides can either be contact or systemic. A contact fungicide kills fungi when sprayed on its surface. A systemic fungicide has to be absorbed by the fungus before the fungus dies. Examples for suitable fungicides, according to the present invention, encompass the following chemical classes and corresponding examples:

Aminopyrimidines such as bupirimate,
Anilinopyrimidines such as cyprodinil, mepanipyrim, pyrimethanil,
Heteroaromatics such as hymexazol,
Heteroaromatic hydrocarbons such as etridiazole,
Chlorophenyls/Nitroanilines such as chloroneb, dicloran, quintozene, tecnazene, tolclofos-methyl,
Benzamide fungicides such as zoxamide,
Benzenesulfonamides such as flusulfamide,
Benzimidazoles such as acibenzolar, benomyl, benzothiazole, carbendazim, fuberidazole, metrafenone, probenazole, thiabendazole, triazoxide, and benzimidazole precursor fungicides,
Carbamates such as propamocarb, diethofencarb,
Carboxamides such as boscalid, diclocymet, ethaboxam, flutolanil, penthiopyrad, thifluzamide
Chloronitriles such chlorothalonil,
Cinnamic acid amides such as dimethomorph, flumorph,
Cyanoacetamide oximes such as cymoxanil,
Cyclopropancarboxamides such as carpropamid,
Dicarboximides such as iprodione, octhilinone, procymidone, vinclozolin
Dimethyldithiocarbamates such ferbam, metam, thiram, ziram,
Dinitroanilines such as fluazinam,
Dithiocarbamates such as mancopper, mancozeb, maneb, metiram, nabam, propineb, zineb,
Dithiolanes such as isoprothiolane,
Glucopyranosyl antibiotics such as streptomycin, validamycin,
Guanidines such as dodine, guazatine, iminoctadine,
Hexopyranosyl antibiotics such as kasugamycin,
Hydroxyanilides such as fenhexamid,
Imidazoles such as imazalil, oxpoconazole, pefurazoate, prochloraz, triflumizole,
Imidazolinones such as fenamidone,
Inorganics such as Bordeaux mixture, copper hydroxide, copper naphthenate, copper oleate, copper oxychloride, copper(II) sulfate, copper sulfate, copper(II) acetate, copper(II) carbonate, cuprous oxide, sulfur,
Isobenzofuranones such as phthalide,
Mandelamides such as mandipropamide,
Morpholines such as dodemorph, fenpropimorph, tridemorph, fenpropidin, piperalin, spiroxamine, aldimorph
Organotins such as fentin,
Oxazolidinones such as oxadixyl,
Phenylamides such as benalaxyl, benalaxyl-M, furalaxyl, metalaxyl, metalaxyl-M, ofurace,
Phenylpyrazoles such as fipronil,
Phenylpyrroles such as fludioxonil,
Phenylureas such as pencycuron,
Phosphonates such fosetyl,
Phthalamic acids such as tecloftalam,
Phthalimides such as captafol, captan, folpet,
Piperazines such as triforine,
Propionamides such as fenoxanil, Pyridines such as pyrifenox,
Pyrimidines such as fenarimol, nuarimol,
Pyrroloquinolinones such as pyroquilon,
Qils such as cyazofamid,
Quinazolinones such as proquinazid,
Quinolines such as quinoxyfen,
Quinones such as dithianon,
Sulfamides such as tolylfluanid, dichlofluanid,
Strobilurines such as azoxystrobin, dimoxystrobin, famoxadone, fluoxastrobin, kresoxim-methyl, metominostrobin, picoxystrobin, pyraclostrobin, trifloxystrobin, orysastrobin,
Thiocarbamates such as methasulfocarb,
Thiophanates such as thiophanate-methyl,
Thiophencarboxamides such silthiofam,
Triazole fungicides such as azaconazole, bitertanol, bromuconazole, cyproconazole, difenoconazole, diniconazole, epoxiconazole, fenbuconazole, fluquinconazole, flusilazole, flutriafol, fluotrimazole, hexaconazole, imibenconazole, ipconazole, metconazole, myclobutanil, penconazole, propiconazole, prothioconazole, simeconazole, tebuconazole, tetraconazole, triadimefon, triadimenol, triticonazole, quinconazole
Triazolobenzothidazoles such as tricyclazole,
Valinamide carbamates such as iprovalicarb, benthiavalicarb
Fluopicolide
Pentachlorophenol
and their mixtures.

c) Herbicides

An herbicide is a pesticide used to kill unwanted plants. Selective herbicides kill specific targets while leaving the desired crop relatively unharmed. Some of these act by interfering with the growth of the weed and are often based on plant hormones. Herbicides used to clear waste ground are nonselective and kill all plant material with which they come into contact. Herbicides are widely used in agriculture and in landscape turf management. They are applied in total vegetation control (TVC) programs for maintenance of highways and railroads. Smaller quantities are used in forestry, pasture systems, and management of areas set aside as wildlife habitat. In general, active ingredients representing including various chemical classes and corresponding examples can be used Anilides such as propanil
Aryloxycarboxylic acids e.g. MCPA-thioethyl
Aryloxyphenoxypropionates e.g. clodinafop-propargyl, cyhalofop-butyl, diclofops, fluazifops, haloxyfops, quizalofops,
Chloroacetamides e.g. acetolochlor, alachlor, butachlor, dimethenamid, metolachlor, propachlor
Cyclohexanedione oximes e.g. clethodim, sethoxydim, tralkoxydim,
Benzamides such as isoxaben
Benzimidazoles such as dicamba, ethofumesate
Dinitroanilines e.g. trifluralin, pendimethalin,
Diphenyl ethers e.g. aclonifen, oxyfluorfen,
The glycine derivative glyphosate, a systemic nonselective (it kills any type of plant) herbicide used in no-till burndown and for weed control in crops that are genetically modified to resist its effects,
Hydroxybenzonitriles e.g. bromoxynil,
Imidazolinones e.g. fenamidone, imazapic, imazamox, imazapic, imazapyr, imazaquin,
Isoxazolidinones e.g. clomazone
Paraquat as bypyridylium,
Phenyl carbamates e.g. desmedipham, phenmedipham,
Phenylpyrazoles e.g. pyraflufen-ethyl
Phenylpyrazolines e.g. pinoxaden,
Pyridinecarboxylic acids or synthetic auxins e.g. picloram, clopyralid, and triclopyr,
Pyrimidinyloxybenzoics e.g. bispyrtbac-sodium
Sulfonyureas e.g. amidosulfuron, azimsulfuron, bensulfuron-methyl, chlorsulfuron, flazasulfuron, foramsulfuron, flupyrsulfuron-methyl-sodium, nicosulfuron, rimsulfuron, sulfosulfuron, tribenuron-methyl, trifloxysurlfuron-sodium, triflusulfuron, tritosulfuron,
Triazolopyrimidines e.g. penoxsulam, metosulam, florasulam,
Triketones e.g. mesotriones, sulcotrione,
Ureas e.g. diuron, linuron,
Phenoxycarboxylic acids such as 2,4-D, MCPA, MCPB, mecoprops,
Triazines such as atrazine, simazine, terbuthylazine,
and their mixtures.

d) Insecticides

An insecticide is a pesticide used against insects in all developmental forms. They include ovicides and larvicides used against the eggs and larvae of insects. Insecticides are used in agriculture, medicine, industry and the household. In the following, suitable chemical classes and examples of insecticides are mentioned:

Abamectin, emamectin,
Anthranilic diamides such as rynaxypyr
Synthetic auxins Duch as avermectin,
Amidines such as amitraz,
Anthranilic diamide Duch as rynaxypyr,
Carbamates such as aldicarb, carbofuran, carbaryl, methomyl, 2-(1-methylpropyl)phenyl methylcarbamate,
Chlorinated insecticides such as, for example, Camphechlor, DDT, Hexachlorocyclohexane, gamma-Hexachlorocyclohexane, Methoxychlor, Pentachlorophenol, TDE, Aldrin, Chlordane, Chlordecone, Dieldrin, Endosulfan, Endrin, Heptachlor, Mirex,
Juvenile hormone mimics such as pyriproxyfen,
Neonicotinoids such as imidacloprid, clothianidin, thiacloprid, thiamethoxam,
Organophosphorus compounds such as acephate, azinphos-methyl, bensulide, chlorethoxyfos, chlorpyrifos, chlorpyriphos-methyl, diazinon, dichlorvos (DDVP), dicrotophos, dimethoate, disulfoton, dthoprop, fenamiphos, fenitrothion, fenthion, fosthiazate, malathion, methamidophos, methidathion, methyl-parathion, mevinphos, naled, omethoate, oxydemeton-methyl, parathion, phorate, phosalone, phosmet, phostebupirim, pirimiphos-methyl, profenofos, terbufos, tetrachlorvinphos, tribufos, trichlorfon,
Oxadiazines such as indoxacarb,
Plant toxin derived compounds such as derris (rotenone), pyrethrum, neem (azadirachtin), nicotine, caffeine,
Pheromones such cuellure, methyl eugenol,
Pyrethroids such as, for example, allethrin, bifenthrin, deltamethrin, permethrin, resmethrin, sumithrin, tetramethrin, tralomethrin, transfluthrin,
Selective feeding blockers such as flonicamid, pymetrozine,
Spinosyns e.g. spinosad
and their mixtures.

e) Plant Growth Regulators

Plant hormones (also known as phytohormones) are chemicals that regulate plant growth. Plant hormones are signal molecules produced within the plant, and occur in extremely low concentrations. Hormones regulate cellular processes in targeted cells locally and when moved to other locations, in other locations of the plant. Plants, unlike animals, lack glands that produce and secrete hormones. Plant hormones shape the plant, affecting seed growth, time of flowering, the sex of flowers, senescence of leaves and fruits. They affect which tissues grow upward and which grow downward, leaf formation and stem growth, fruit development and ripening, plant longevity and even plant death. Hormones are vital to plant growth and lacking them, plants would be mostly a mass of undifferentiated cells. In the following, suitable plant growth regulators are mentioned:

Aviglycine,

Cyanamide,

Gibberellins such gibberellic acid,

Quaternary ammoniums such as chlormequat chloride, mepiquat chloride,

Ethylene generators such ethephone, f) Rodenticides

Rodenticides are a category of pest control chemicals intended to kill rodents. Rodents are difficult to kill with poisons because their feeding habits reflect their place as scavengers. They would eat a small bit of something and wait, and if they do not get sick, they would continue eating. An effective rodenticide must be tasteless and odorless in lethal concentrations, and have a delayed effect. In the following, examples for suitable rodenticides are given:

Anticoagulants are defined as chronic (death occurs after 1-2 weeks post ingestion of the lethal dose, rarely sooner), single-dose (second generation) or multiple dose (first generation) cumulative rodenticides. Fatal internal bleeding is caused by lethal dose of anticoagulants such as brodifacoum, coumatetralyl or warfarin. These substances in effective doses are antivitamins K, blocking the enzymes $K_1$-2,3-epoxide-reductase (this enzyme is preferentially blocked by 4-hydroxycoumarin/4-hydroxythiacoumarin derivatives) and $K_1$-quinone-reductase (this enzyme is preferentially blocked by indandione derivatives), depriving the organism of its source of active vitamin $K_1$. This leads to a disruption of the vitamin K cycle, resulting in an inability of production of essential blood-clotting factors (mainly coagulation factors II (prothrombin), VII (proconvertin), IX (Christmas factor) and X (Stuart factor)). In addition to this specific metabolic disruption, toxic doses of 4-hydroxycoumarin/4-hydroxythiacoumarin and indandione anticoagulants are causing damage to tiny blood vessels (capillaries), increasing their permeability, causing diffuse internal bleedings (haemorrhagias). These effects are gradual; they develop in the course of days and are not accompanied by any nociceptive perceptions, such as pain or agony. In the final phase of intoxication the exhausted rodent collapses in hypovolemic circulatory shock or severe anemia and dies calmly. Rodenticidal anticoagulants are either first generation agents (4-hydroxycoumarin type: warfarin, coumatetralyl; indandione type: pindone, diphacinone, chlorophacinone), generally requiring higher concentrations (usually between 0.005 and 0.1%), consecutive intake over days in order to accumulate the lethal dose, poor active or inactive after single feeding and less toxic than second generation agents, which are derivatives of 4-hydroxycoumarin (difenacoum, brodifacoum, bromadiolone and flocoumafen) or 4-hydroxy-1-benzothiin-2-one (4-hydroxy-1-thiacoumarin, sometimes incorrectly referred to as 4-hydroxy-1-thiocoumarin, for reason see heterocyclic compounds), namely difethialone. Second generation agents are far more toxic than first generation agents, they are generally applied in lower concentrations in baits (usually in the order of 0.001-0.005%), and are lethal after single ingestion of bait and are effective also against strains of rodents that have become resistant against first generation anticoagulants; thus the second generation anticoagulants are sometimes referred to as "superwarfarins". Sometimes, anticoagulant rodenticides are potentiated by an antibiotic, most commonly by sulfaquinoxaline. The aim of this association (e.g. warfarin 0.05%+sulfaquinoxaline 0.02%, or difenacoum 0.005%+sulfaquinoxaline 0.02% etc.) is that the antibiotic/bacteriostatic agent suppresses intestinal/gut symbiotic microflora that represents a source of vitamin K. Thus the symbiotic bacteria are killed or their metabolism is impaired and the production of vitamin K by them is diminuted, an effect which logically contributes to the action of anticoagulants. Antibiotic agents other than sulfaquinoxaline may be used, for example co-trimoxazole, tetracycline, neomycin or metronidazole. A further synergism used in rodenticidal baits is that of an association of an anticoagulant with a compound with vitamin D-activity, i.e. cholecalciferol or ergocalciferol (see below). A typical formula used is, e.g., warfarin 0.025-0.05%+cholecalciferol 0.01%. In some countries there are even fixed three-component rodenticides, i.e. anticoagulant+antibiotic+vitamin D, e.g. difenacoum 0.005%+sulfaquinoxaline 0.02%+cholecalciferol 0.01%. Associations of a second-generation anticoagulant with an antibiotic and/or vitamin D are considered to be effective even against the most resistant strains of rodents, though some second generation anticoagulants (namely brodifacoum and difethialone), in bait concentrations of 0.0025-0.005% are so toxic that no known resistant strain of rodents exists and even rodents resistant against any other derivatives are reliably exterminated by application of these most toxic anticoagulants.

Vitamin $K_1$ has been suggested and successfully used as an antidote for pets or humans, which/who were either accidentally or intentionally (poison assaults on pets, suicidal attempts) exposed to anticoagulant poisons. In addition, since some of these poisons act by inhibiting liver functions and in progressed stages of poisoning, several blood-clotting factors as well as the whole volume of circulating blood lacks, a blood transfusion (optionally with the clotting factors present) can save a person's life who inadvertently takes them, which is an advantage over some older poisons.

Metal phosphides have been used as a means of killing rodents and are considered single-dose fast acting rodenticides (death occurs commonly within 1-3 days after single bait ingestion). A bait consisting of food and a phosphide (usually zinc phosphide) is left where the rodents can eat it. The acid in the digestive system of the rodent reacts with the phosphide to generate the toxic phosphine gas. This method of vermin control has possible use in places where rodents are resistant to some of the anticoagulants, particularly for control of house and field mice; zinc phosphide baits are also cheaper than most second-generation anticoagulants, so that sometimes, in cases of large infestation by rodents, their population is initially reduced by copious amounts of zinc phosphide bait applied, and the rest of the population that survived the initial fast-acting poison is then eradicated by prolonged feeding on anticoagulant bait. Inversely, the individual rodents that survived anticoagulant bait poisoning (rest population) can be eradicated by pre-baiting them with nontoxic bait for a week or two (this is important to overcome bait shyness, and to get rodents used to feeding in specific areas by offering specific food, especially when eradicating rats) and subsequently applying poisoned bait of the same sort as used for pre-baiting until all consumption of the bait ceases (usually within 2-4 days). These methods of alternating rodenticides with different modes of action provides a factual or an almost 100% eradication of the rodent population in the area if the acceptance/palatability of bait is good (i.e., rodents readily feed on it).

Phosphides are rather fast acting rat poisons, resulting in that the rats are dying usually in open areas instead of the affected buildings. Typical examples are aluminum phosphide (fumigant only), calcium phosphide (fumigant only), magnesium phosphide (fumigant only) and zinc phosphide (in baits). Zinc phosphide is typically added to rodent baits in amounts of around 0.75-2%. The baits have a strong, pungent garlic-like odor characteristic for phosphine liberated by hydrolysis. The odor attracts (or, at least, does not repulse) rodents, but has a repulsive effect on other mammals; birds, however (notably wild turkeys), are not sensitive to the smell and feed on the bait thus becoming collateral damage.

Hypercalcemia. Calciferols (vitamins D), cholecalciferol (vitamin $D_3$) and ergocalciferol (vitamin $D_2$) are used as rodenticides, which are toxic to rodents for the same reason that they are beneficial to mammals: they are affecting calcium and phosphate homeostasis in the body. Vitamins D are essential in minute quantities (few IUs per kilogram body weight daily, which is only a fraction of a milligram), and like most fat soluble vitamins they are toxic in larger doses as they readily result in the so-called hypervitaminosis, which is, simply said, poisoning by the vitamin. If the poisoning is severe enough (that is, if the dose of the toxicant is high enough), it eventually leads to death. In rodents consuming the rodenticidal bait it causes hypercalcemia by raising the calcium level, mainly by increasing calcium absorption from food, mobilising bone-matrix-fixed calcium into ionised form (mainly monohydrogencarbonate calcium cation, partially bound to plasma proteins, $[CaHCO_3]^+$), which circulates dissolved in the blood plasma, and after ingestion of a lethal dose the free calcium levels are raised sufficiently so that blood vessels, kidneys, the stomach wall and lungs are mineralised/calcificated (formation of calcificates, crystals of calcium salts/complexes in the tissues thus damaging them), leading further to heart problems (myocard is sensitive to variations of free calcium levels that are affecting both myocardial contractibility and excitation propagation between atrias and ventriculas) and bleeding (due to capillary damage) and possibly kidney failure. It is considered to be single-dose, or cumulative (depending on concentration used; the common 0.075% bait concentration is lethal to most rodents after a single intake of larger portions of the bait), sub-chronic (death occurring usually within days to one week after ingestion of the bait). Applied concentrations are 0.075% cholecalciferol and 0.1% ergocalciferol when used alone. There is an important feature of calciferols toxicology which is that they are synergistic with anticoagulant toxicants. This means that mixtures of anticoagulants and calciferols in the same bait are more toxic than the sum of toxicities of the anticoagulant and the calciferol in the bait so that a massive hypercalcemic effect can be achieved by substantially lower calciferol content in the bait and vice-versa. More pronounced anticoagulant/hemorrhagic effects are observed if calciferol is present. This synergism is mostly used in baits low in calciferol because effective concentrations of calciferols are more expensive than effective concentrations of most anticoagulants. The historically very first application of a calciferol in rodenticidal bait was, in fact, the Sorex product Sorexa® D (with a different formula than today's Sorexa® D) back in the early 1970's, containing warfarin 0.025%+ergocalciferol 0.1%. Today, Sorexa® CD contains a 0.0025% difenacoum+ 0.075% cholecalciferol combination. Numerous other brand products containing either calciferols 0.075-0.1% (e.g. Quintox®, containing 0.075% cholecalciferol) alone, or a combination of calciferol 0.01-0.075% with an anticoagulant are marketed.

g) Miticides, Moluscicides and Nematicides

Miticides are pesticides that kill mites. Antibiotic miticides, carbamate miticides, formamidine miticides, mite growth regulators, organochlorine, permethrin and organophosphate miticides all belong to this category. Molluscicides are pesticides used to control mollusks, such as moths, slugs and snails. These substances include metaldehyde, methiocarb and aluminium sulfate. A nematicide is a type of chemical pesticide used to kill parasitic nematodes (a phylum of worm). A nematicide is obtained from a neem tree's seed cake; which is the residue of neem seeds after oil extraction. The neem tree is known by several names in the world but was first cultivated in India since ancient times.

h) Antimicrobials

In the following examples, antimicrobials suitable for agrochemical compositions according to the present invention are given. Bactericidal disinfectants mostly used are those applying active chlorine (i.e., hypochlorites, chloramines, dichloroisocyanurate and trichloroisocyanurate, wet chlorine, chlorine dioxide, etc.), active oxygen (peroxides such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols are used), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants such as some quaternary ammonium cations (such as benzalkonium chloride, cetyl trimethylammonium bromide or chloride, didecyldimethylammonium chloride, cetylpyridinium chloride, benzethonium chloride) and others, non-quarternary compounds such as chlorhexidine, glucoprotamine, octenidine dihydrochloride, etc.), strong oxidizers such as ozone and permanganate solutions;

heavy metals and their salts such as colloidal silver, silver nitrate, mercury chloride, phenylmercury salts, copper sulfate, copper oxide-chloride etc. Heavy metals and their salts are the most toxic and environmentally hazardous bactericides and, therefore, their use is strongly suppressed or forbidden; further, also properly concentrated strong acids (phosphoric, nitric, sulfuric, amidosulfuric, toluenesulfonic acids) and alcalis (sodium, potassium, calcium hydroxides) between pH<1 or >13, particularly below elevated temperatures (above 60° C.) kill bacteria.

As antiseptics (i.e., germicide agents that can be used on human or animal body, skin, mucoses, wounds and the like), few of the above mentioned disinfectants can be used under proper conditions (mainly concentration, pH, temperature and toxicity toward man/animal). Among them, important are Some properly diluted chlorine preparations (e.g. Daquin's solution, 0.5% sodium or potassium hypochlorite solution, pH-adjusted to pH 7-8, or 0.5-1% solution of sodium benzenesulfochloramide (chloramine B)), some iodine preparations such as iodopovidone in various galenics (ointments, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid some phenolic compounds such as hexachlorophene, triclosan and Dibromol, and cation-active compounds such as 0.05-0.5% benzalkonium, 0.5-4% chlorhexidine, 0.1-2% octenidine solutions.

Bactericidal antibiotics kill bacteria; bacteriostatic antibiotics only slow down their growth or reproduction. Penicillin is a bactericide, as are cephalosporins. Aminoglycosidic antibiotics can act in both a bactericidic manner (by disrupting cell wall precursor leading to lysis) or bacteriostatic manner (by connecting to 30 s ribosomal subunit and reducing translation fidelity leading to inaccurate protein synthesis). Other bactericidal antibiotics according to the present invention include the fluoroquinolones, nitrofurans, vancomycin, monobactams, co-trimoxazole, and metronidazole Preferred actives are those with systemic or partially systemic mode of action such as for example azoxystrobin.

Overall preferred are biocides selected either (i) from the group consisting of azoles, strobilurines, diphenyl ethers, anilides, organophosphates, synthetic pyrethroids, neonicotinoids, oxadiazines, benzoylureas, phenyl carbamates, chloroacetamides, triketones, pyridinecarboxylic acids, cyclohexanedione oximes, phenylpyrazoles, glyphosate and its salts, and their mixtures, or (ii) from the group consisting of oxyfluorofen, propanil, chlorpyrifos, bifenthrin, deltamethrin, azoxystrobin, krexoxim-methyl, lambda-cyhalothrin, novaluron, lufenuron, imidacloprid, thiacloprid, indoxacarb, oxyfluorfen, fluoroxypyr and its esters, phenmedipham, desmedipham, acetochlor, tebuconazole, epoxiconazole, propiconazole, fenbuconazole, triademenol, fipronil, and their mixtures.

Oil Components or Co-Solvents

Suitable oil components or co-solvents (component c) are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms (Cetiol® B) or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Cetiol® AB), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.), aliphatic or naphthenic hydrocarbons, such as, for example, squalane, squalene or dialkylcyclohexanes, and/or mineral oils.

The preferred oil components or co-solvents show an ester structure. Particularly preferred are adipates (Cetiol® B, Agnique® DiME 6), lactates, methyl esters of vegetable oils (Agnique ME 18RD-F, Agnique® ME 12C-F), alkyl esters (Agnique® Ae 3-2EH=2-EthylHexyl Lactate)—all products available in the market from Cognis GmbH, Düsseldorf.

Emulsifiers

Suitable emulsifiers (component d) include non-ionic and anionic surfactants and their mixtures. Non-ionic surfactants include for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol,
polyalkylene glycols and The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

a) Partial Glycerides

Typical examples of suitable partial glycerides are hydroxystearic acid monoglyceride, hydroxyystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30, and preferably 5 to 10, mol ethylene oxide onto the partial glycerides mentioned are also suitable.

b) Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30, and preferably 5 to 10, mol ethylene oxide onto the sorbitan esters mentioned are also suitable.

c) Alk(en)yl Oligoglycosides

The alkyl or alkenyl oligoglycosides representing also preferred emulsifiers may be derived from aldoses or ketoses containing 5 or 6 carbon atoms, preferably glucose. Accordingly, the preferred alkyl and/or alkenyl oligoglycosides are alkyl or alkenyl oligoglucosides. These materials are also known generically as "alkyl polyglycosides" (APG). The alk (en)yl oligoglycosides according to the invention correspond to formula (IV):

$$R^4O[G]_p \quad (IV)$$

wherein $R^4$ is an alkyl or alkenyl radical having from 6 to 22 carbon atoms, G is a sugar unit having 5 or 6 carbon atoms and p is a number from 1 to 10. The index p in general formula (II) indicates the degree of oligomerisation (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is mostly a broken number. Alk(en)yl oligoglycosides having an average degree of oligomerisation p of 1.1 to 3.0 are preferably used. Alk(en)yl oligoglycosides having a degree of oligomerisation below 1.7 and, more particularly, between 1.2 and 1.4 are preferred from the applicational point of view. The alkyl or alkenyl radical $R^5$ may be derived from primary alcohols containing 4 to 22 and preferably 8 to 16 carbon atoms. Typical examples are butanol, caproic alcohol, caprylic alcohol, capric alcohol, undecyl alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof such as are formed, for example, in the hydrogenation of technical fatty acid methyl esters or in the hydrogenation of aldehydes from Roelen's oxo synthesis. Alkyl oligoglucosides based on hydrogenated $C_8$-$C_{16}$ coconut oil alcohol having a DP of 1 to 3 are preferred. Also suitable are alkoxylation products of alkyl oligoglucosides, for example adducts of 1 to 10 moles ethylene oxide and/or 1 to 5 moles propylene oxide to $C_8$-$C_{10}$ or $C_{12}$-$C_{18}$ alkyl oligoglucoside having a DP between 1.2 and 1.4.

d) Alkoxylated Vegetable Oils

Suitable emulsifiers are castor oil, rape seed oil, soy been oil ethoxylated with 3 to 80 moles ethylene oxide (Agnique® CSO 35, Agnique® SBO 10, Agnique® SBO 60))

e) Alkoxylated Copolymers

Typical copolymers are ethoxylated and propoxylated block and/or random polymers of $C_2$-$C_{22}$ linear or branched alcohols.

f) Anionic Emulsifiers

Typical anionic emulsifiers encompass alkylbenzene sulfonic acids and their salts, as for example calcium dodecylbenzene sulfonate dissolved in isobutanol (Agnique® ABS 65C) or 2-ethylhexanol (Agnique® ABS 60C-EH), dialkyl sulfosuccinates, as for example di-2-ethylhexyl sulfosuccinate or dioctyl sulfosuccinate, and polyacrylates having a molar weight of from 1,000 to 50,000.

g) Miscellaneous Emulsifiers

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Biocide Compositions

Depending on the nature of the biocide the products may show the following compositions:

(a) about 0.1% b.w. to about 99% b.w., preferably about 15% b.w. to about 70% b.w., and most preferably about 20% b.w. to about 45% b.w. alkoxylated oligoglycerol esters;
(b) about 1% b.w. to about 99.1% b.w., preferably about 5% b.w. to about 75% b.w., and most preferably about 15% b.w. to about 40% b.w. biocides;
(c) 0 to about 50% b.w., preferably about 5% b.w. to about 30% b.w. and more preferably about 10% b.w. to about 25% b.w. oil components or co-solvents and
(d) 0 to about 15% b.w., and preferably about 5% b.w. to about 10% b.w., emulsifiers on the condition that the numbers optionally together with water add to 100% b.w. The compositions represent concentrates to be diluted with water to give aqueous formulations for end-users comprising about 0.5 to about 5, preferably about 0.5 to about 1% of the active matter represented by the concentrate.

INDUSTRIAL APPLICATION

Another embodiment of the present invention is related to the use of alkoxylated oligoglycerol esters as adjuvants for biocides. Typically, the esters are used in tank mix or in can formulation in combination with a biocide, preferably a fungicide at a dose rate of about 20 and about 2.000, preferably about 40 to about 500 g/ha adjuvant. As shown by the following greenhouse examples an optimised product is able to boost a standard biocide formulation in a sub lethal dose from approximately 50% control up to more than 95% control.

EXAMPLES

Example 1

Synthesis of Diglycerol High Oleic Sunflower Fatty Acid Monoester

One mole technical statistic diglycerol+10EO, 1 mole HOSO-ME (High-oleic sunflower fatty acid methyl ester), and 55 g potassium hypophosphite (25% b.w. in methanol) were placed in a flask. The mixture was heated up slowly under stirring to 220° C. The reaction started vigorously at a temperature of about 160 to 180° C. After removing the first major amount of methanol, the vacuum was slowly reduced to less than 1 mbar and the reaction mixture kept under these conditions for another 3 to 4 hours. Once the reaction was completed the product was cooled down without any additional purification. 870 g diglycerol sunflower fatty acid monoester were obtained as a clear yellow liquid.

Example 2

Synthesis of Diglycerol Oleic Acid Diester 130 g diglycerol+10EO, 120 g technical oleic acid (Edenor® Ti05, Emery Oleochemicals), and 1.7 g hypophosphorous acid were placed in a flask and heated up under vigorous stirring to 240° C. The flask was set under nitrogen atmosphere. After the removal of water the ester was cooled down without any additional purification. 240 g diglycerol oleic acid diester were obtained as a clear yellowish liquid.

Examples 3 and 4

The following tables 1 and 2 provide storage stable formulations comprising alkoxylated oligoglycerol esters according to the present invention. The composition according to Table 1 was wet milled according to standard procedures and showed a particle size (D95) of less than 10 µm. Composition 2 was stirred until a stable formulation was obtained.

TABLE 1

Storage stable SC formulation of Azoxystrobin

| Amount [g] | Product | Chemical name |
|---|---|---|
| 250 | | Azoxystrobin |
| 100 | | Glycerol |
| 150 | | Diglycerol ester according to Example 2 |
| 20 | Hydropalat ® 5040 | |
| 100 | Sovermol ® 820 | |
| 380 | | Water |

TABLE 2

EC-formulation of Chlorpyrifos

| Amount [g] | Product | Chemical name |
|---|---|---|
| 46 | | Chlorpyrifos |
| 20 | Agnique ® AMD 810 | |
| 10 | Agnique ® ME 890 | |
| 8 | Agnique ® ABS 70 C | |
| 16 | | Diglycerol ester according to Example 2 |

Examples 5 to 14

Greenhouse Trials

The adjuvant performance of different alkoxylated and non-alkoxylated diglycerol esters were tested in combination with two commercially available biocide compositions Amistar® SC 250 (Syngenta, active: strobilurin) and Opus® SC 125 (BASF, active: epoxiconazole) in greenhouse trials. The adjuvants were added as tank mix adjuvants to the biocide in amounts of 5% b.w. As test method the Barley Segment Test with powdery mildew as the pathogenic species was used. The results are shown in Tables 3 and 4. Examples 5 to 14 are according to the invention, examples C1 to C10 serve for comparison.

TABLE 3

Adjuvant effects on strobilurin

| Example | Biocide + Adjuvant | Powdery mildew infection (%) |
|---|---|---|
| | Amistar ® (alone) | 59 |
| 5 | + Diglycerol + 10EO oleyl tetraester | 9 |
| 6 | + Diglycerol + 10EO oleyl diester | 2 |
| 7 | + Diglycerol + 10EO oleyl monoester | 4 |
| 8 | + Diglycerol + 10EO linseed monoester | 9 |
| 9 | + Diglycerol + 10EO sunflower monoester | 12 |
| C1 | + Diglycerol oleyl tetraester | 29 |
| C2 | + Diglycerol oleyl diester | 25 |
| C3 | + Diglycerol oleyl monoester | 21 |

TABLE 3-continued

Adjuvant effects on strobilurin

| Example | Biocide + Adjuvant | Powdery mildew infection (%) |
|---|---|---|
| C4 | + Diglycerol linseed monoester | 25 |
| C5 | + Diglycerol sunflower monoester | 31 |

TABLE 4

Adjuvant effects on epoxiconazole

| Example | Biocide + Adjuvant | Powdery mildew infection (%) |
|---|---|---|
|  | Opus ® (alone) | 36 |
| 10 | + Diglycerol + 10EO oleyl tetra ester | 19 |
| 11 | + Diglycerol + 10EO oleyl diester | 14 |
| 12 | + Diglycerol + 10EO oleyl monoester | 19 |
| 13 | + Diglycerol + 10EO linseed monoester | 19 |
| 14 | + Diglycerol + 10EO sunflower monoester | 11 |
| C6 | + Diglycerol oleyl tetraester | 28 |
| C7 | + Diglycerol oleyl diester | 25 |
| C8 | + Diglycerol oleyl monoester | 25 |
| C9 | + Diglycerol linseed monoester | 24 |
| C10 | + Diglycerol sunflower monoester | 24 |

All adjuvants turned out to boost both the strobilurin and the epoxiconazole. However, outstanding results were achieved with a Diglycerolester comprising two oleyl groups. It was also shown that the alkoxylated esters show a superior performance over the non-alkoxylated species known from the state of the art.

The invention claimed is:

1. A biocide composition comprising:
(a) an alkoxylated diglycerol ester of an unsaturated fatty acid;
(b) an agrochemical biocide, and
(c) optionally an oil component or co-solvent and/or
(d) an emulsifier,
wherein component (a) comprises an alkoxylated diglycerol ester according to general formula (I)

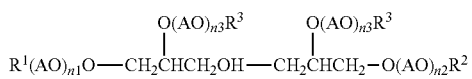

in which $R^1$, $R^2$ and $R^3$ independently represent either hydrogen or an unsaturated, linear or branched and optionally hydroxy substituted acyl radical having 2 to 22 carbon atoms and up to three double bonds on condition that at least one of the groups $R^1$, $R^2$ and $R^3$ is different from hydrogen, AO stands for an alkylene oxide unit selected from ethylene oxide, propylene oxide, butylene oxide and their mixtures, and n1, n2 and n3 independently mean integers in the range from 1 to 100 on condition that the sum (n1+n2+n3) is an integer in the range of 10 to 200,
and wherein component (b) is selected from the group consisting of herbicides, fungicides, insecticides, and plant growth regulators.

2. The biocide composition according to claim 1 wherein component (a) comprises an ethoxylated diglycerol ester.

3. The biocide composition according to claim 1, wherein component (a) comprises an alkoxylated diglycerol ester derived from unsaturated vegetable fatty acids.

4. The biocide composition according to claim 1, wherein the biocide (component b) is selected from the group consisting of azoles, strobilurines, diphenyl ethers, anilides, organophosphates, synthetic pyrethroids, neonicotinoids, oxadiazines, benzoylureas, phenyl carbamates, chloroacetamides, triketones, pyridinecarboxylic acids, cyclohexanedione oximes, phenylpyrazoles, glyphosate and its salts, and their mixtures.

5. The biocide composition according to claim 1, wherein the biocide (component b) is selected from the group consisting of oxyfluorofen, propanil, chlorpyrifos, bifenthrin, deltamethrin, azoxystrobin, krexoxim-methyl, lambda-cyhalothrin, novaluron, lufenuron, imidacloprid, thiacloprid, indoxacarb,oxyfluorfen, fluoroxypyr and its esters, phenmedipham, desmedipham, acetochlor, tebuconazole, epoxiconazole, propiconazole, fenbuconazole, triademenol, fipronil, and their mixtures.

6. The biocide composition according to claim 1, comprising an oil component or a co-solvent (component c) that is selected from the group consisting of Guerbet alcohols based on fatty alcohols having 6 to 18 carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, methyl esters of $C_6$-$C_{22}$ fatty acids, esters of linear $C_6$-$C_{22}$-fatty acids with branched alcohols, esters of $C_{18}$-$C_{38}$-alkyl hydroxy carboxylic acids with linear or branched $C_6$-$C_{22}$-fatty alcohols, esters of linear and/or branched fatty acids with polyhydric alcohols and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, Guerbet carbonates, based on fatty alcohols having 6 to 18, carbon atoms, esters of monopropylene glycol with $C_2$-$C_{18}$ acids and benzoic acid, esters of benzoic acid with linear and/or branched $C_6$-$C_{22}$-alcohols, linear or branched, symmetrical or asymmetrical dialkyl ethers having 6 to 22 carbon atoms per alkyl group, ring-opening products of epoxidized fatty acid esters with polyols, silicone oils and/or aliphatic or naphthenic hydrocarbons, mineral oils and their mixtures.

7. The biocide composition according to claim 1, comprising an oil component that comprises an ester structure.

8. The biocide composition according to claim 1, comprising an oil component that is selected from the group consisting of adipates, lactates, methyl esters of vegetable oils, and alkyl esters.

9. The biocide composition according to claim 1, comprising an emulsifier (component d) that is selected from the group consisting of non-ionic and anionic surfactants or their mixtures.

10. The biocide composition according to claim 1, comprising:
(a) 0.1 to 99% by weight of the alkoxylated diglycerol ester of an unsaturated fatty acid,
(b) 1 to 99.1% by weight of the biocide,
(c) 0 to 50% by weight of the oil component or the co-solvent and
(d) 0 to 15% by weight of the emulsifier,
on the condition that the numbers add optionally together with water to 100% by weight, based on the weight of the biocide composition.

11. The biocide composition according to claim 1, wherein the unsaturated fatty acid comprises oleic acid, elaidinic acid, linolic acid, linoleic acid, conjugated linoleic acid, ricinoleic acid, or their mixtures.

12. The biocide composition according to claim 1, wherein the unsaturated fatty acid comprises technical grade fatty acid mixtures obtained from sunflower oil, high-oleic sun-flower oil (HOSO), line seed oil, or olive oil.

* * * * *